United States Patent
Gylys et al.

(10) Patent No.: US 7,251,027 B2
(45) Date of Patent: Jul. 31, 2007

(54) REAL TIME IN SITU MONITORING OF A SOLUTION

(75) Inventors: Vytas T. Gylys, Bell Canyon, CA (US); David Stelman, Thousand Oaks, CA (US)

(73) Assignee: The Boeing Company, Chicago, IL (US)

( * ) Notice: Subject to any disclaimer, the term of this patent is extended or adjusted under 35 U.S.C. 154(b) by 138 days.

(21) Appl. No.: 11/131,129

(22) Filed: May 17, 2005

(65) Prior Publication Data
US 2006/0262300 A1   Nov. 23, 2006

(51) Int. Cl.
*G01J 3/44* (2006.01)

(52) U.S. Cl. .................. 356/301; 372/89; 372/55; 372/186.04; 205/556; 205/466

(58) Field of Classification Search ............ 356/301; 372/89, 55; 422/186.04; 205/556, 466
See application file for complete search history.

(56) References Cited

U.S. PATENT DOCUMENTS

| | | | |
|---|---|---|---|
| 5,652,653 A * | 7/1997 | Alsmeyer et al. | ........... 356/301 |
| 5,982,484 A * | 11/1999 | Clarke et al. | ............... 356/301 |
| 6,774,992 B1 * | 8/2004 | Garver et al. | ............... 356/301 |

* cited by examiner

*Primary Examiner*—Gregory J. Toatley, Jr.
*Assistant Examiner*—Abdullahi Nur
(74) *Attorney, Agent, or Firm*—MacPherson Kwok Chen & Heid LLP; David S. Park

(57) ABSTRACT

A real time in situ system and method for monitoring solutions, such as basic hydrogen peroxide (BHP) and other laser fuel solutions, is provided. Raman spectroscopy is applied to a solution of interest to provide substantially real time and in situ characterization of the solution. In one embodiment, $OOH^-$ and $H_2O_2$ Raman peaks are monitored in real time and in situ for determination of BHP composition.

20 Claims, 4 Drawing Sheets

REAL TIME IN SITU MONITORING OF A SOLUTION

TECHNICAL FIELD

The present invention relates generally to solution monitoring systems and methods and, more particularly, to a laser fuel monitoring system and method.

BACKGROUND

Laser beams are generated by means of a population inversion consisting of an unstable abundance of molecules having excited high energy electronic states which release photons as they decay to the equilibrium lower energy states of the optically active media.

In high energy chemical lasers, the excited electronic states are generated by a chemical reaction. For example, one such reaction involves the use of excited molecular oxygen, hereinafter referred to as singlet delta oxygen (SDO) or $O_2(^1\Delta)$, in combination with an optically active media or lasing substance, such as iodine or fluorine.

One method presently in use for generating a stream of SDO involves a chemical reaction between chlorine gas and a basic solution of hydrogen peroxide, hereinafter referred to as basic hydrogen peroxide (BHP). The excited oxygen can then be added to a suitable lasing medium and the mixture passed through an optical resonator/cavity to bring about a lasing action.

These lasers have been found to be very useful but improved performance characteristics, especially in the area of materials supply and efficiency, is desirable. In particular, a number of problems in the supply, storage, and maintenance of the BHP reactant material has limited the use of these chemical lasers in military and airborne applications.

For example, a high-performance tactical laser weapon requires a laser with rapid fire capability. Many lasers, such as chemical oxygen iodine lasers (COILs) (e.g., the Advanced Tactical Laser (ATL) Advanced Component Technology Demonstration (ACTD)), can operate only in a short lasing burst limited by the supply of BHP. In the ATL, the airborne laser (ABL), and the EC-COIL laser systems, each laser burst is separated by a longer time period during which spent and excess BHP is recycled and/or regenerated to support another lasing burst. This limits the utility of laser weapons and hence their potential.

In order to improve the efficiency of BHP supply via recirculation and/or regeneration, it is essential to provide the laser fuel "status" in real time to permit the user to know the condition of the fuel prior to lasing and during recycling or regeneration. Currently, a system or method for real time in situ monitoring of BHP solution (for concentration or component analysis or diagnostics) is not available. Instead, BHP characterization currently requires batch sampling of BHP before and after reaction followed by titrations to determine the solution content, thereby requiring hours of labor and cost and resulting in great inefficiencies in the BHP supply.

Thus, a real time and in situ system and method for monitoring or analyzing a solution including hydrogen peroxide (e.g., BHP) is highly desirable and advantageous.

SUMMARY

The present invention advantageously applies Raman spectroscopy to a solution including hydrogen peroxide to provide a substantially real time and in situ monitoring system and method for determining characteristics of the solution. In one embodiment, $OOH^-$ and $H_2O_2$ Raman peaks are monitored in real time and in situ for determination of BHP composition.

In accordance with an embodiment of the present invention, a solution monitoring system is provided, the system including a laser for providing excitation photons to a solution, an immersion probe within the solution for transmitting Raman scattered photons, and a spectrometer operably coupled to the immersion probe for measuring the Raman scattered photons transmitted by the immersion probe.

In accordance with another embodiment of the present invention, a laser fuel monitoring system is provided, the system including a laser for providing Raman excitation photons to a solution of basic hydrogen peroxide, and an immersion probe within the solution for delivering the Raman excitation photons from the laser and for transmitting Raman scattered photons from the solution of basic hydrogen peroxide. The system further includes a spectrometer operably coupled to the immersion probe for measuring the Raman scattered photons transmitted by the immersion probe, the spectrometer measuring Raman emission lines at about 845 $cm^{-1}$ for $OOH^-$ and Raman emission lines at about 875 $cm^{-1}$ for $H_2O_2$.

In accordance with yet another embodiment of the present invention, a method for monitoring a laser fuel is provided, the method including providing Raman excitation photons to a solution including hydrogen peroxide, collecting Raman scattered photons from the solution, and monitoring a ratio of Raman emission lines to determine characteristics of the solution.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1:
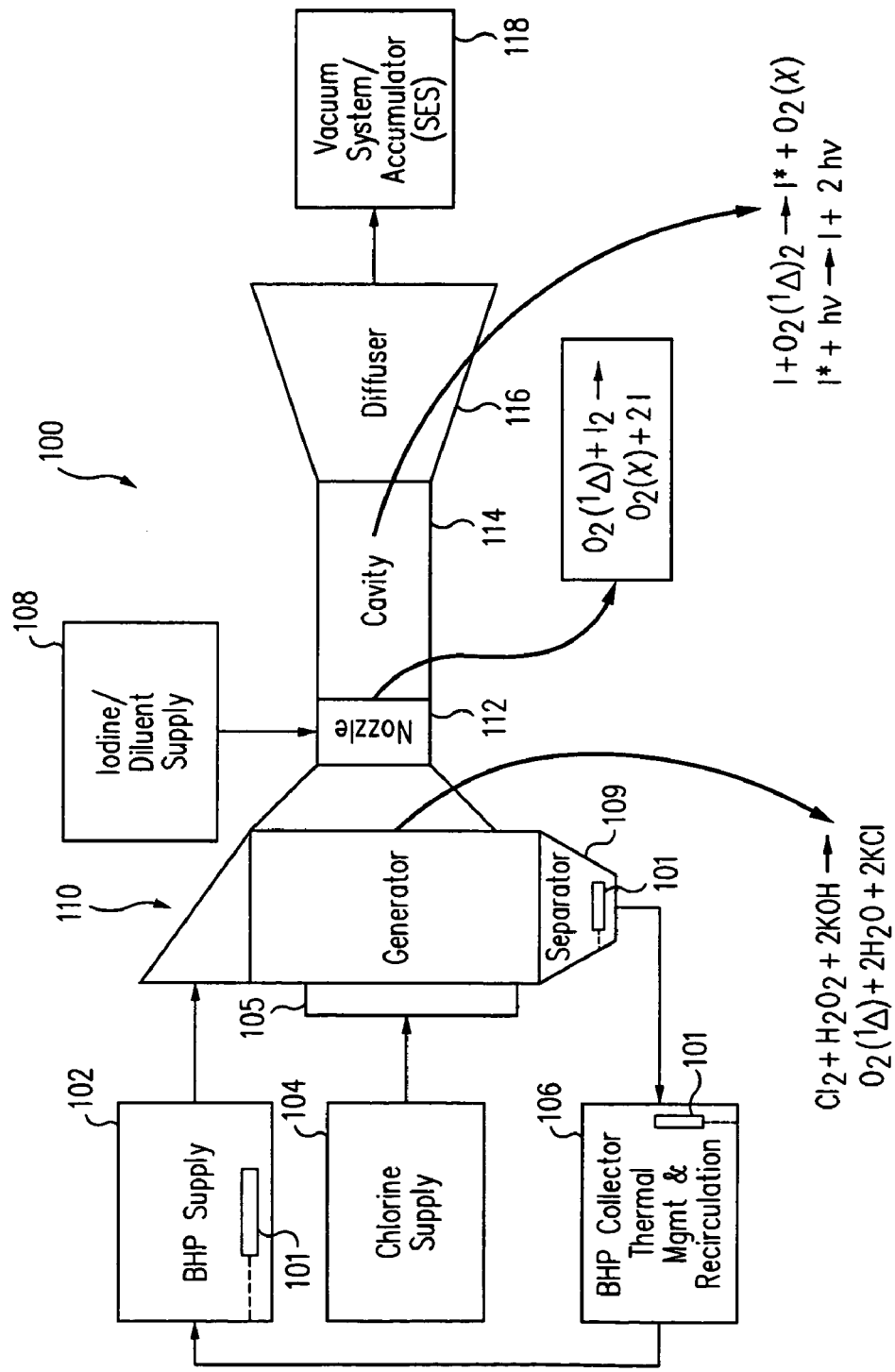
FIG. 1 shows a block diagram illustrating a laser system including a solution monitoring subsystem in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a real time in situ system and method for monitoring solutions including hydrogen peroxide, such as BHP and other laser fuel solutions. Thus, in one example, the present invention may serve as a type of "fuel" meter for laser systems such as the ABL and ATL laser systems. The present invention also permits a means by which the regeneration of BHP with alkaline peroxide by an electro-chemical cell could be monitored in situ and controlled. Advantageously, the present invention provides for cost and time savings and efficiency in providing fuel for laser systems.

FIG. 1 shows a block diagram illustrating a laser system 100 in accordance with an embodiment of the present invention. In one example, system 100 may be a chemical oxygen-iodine laser (COIL). System 100 includes a singlet delta oxygen (SDO or $O_2(^1\Delta)$) generator 110 operably coupled to a basic hydrogen peroxide (BHP) supply 102 and a chlorine supply 104. An outlet of generator 110 is operably coupled to a supersonic nozzle 112, which is also operably coupled to an iodine supply 108. A laser cavity 114 is operably coupled to an outlet of nozzle 112, and a diffuser 116 is operably coupled to an outlet of cavity 114. Finally a sealed exhaust system 118, providing vacuum and accumulation of exhaust gases, is operably coupled to an outlet of diffuser 116.

A gas/liquid separator 109 is operably coupled to generator 110 to separate spent and excess liquid reactants and products (i.e., spent and excess BHP and salts) from gas reactants and products. It is noted that gas/liquid separator 109 may be integral to generator 110 in one embodiment or a separate module in another embodiment. A BHP collector 106, which collects the separated liquid phase from gas/liquid separator 109, is coupled to gas/liquid separator 109. In other embodiments, BHP collector 106 may further treat the separated liquid reactants and BHP (e.g., heat treatment via a heat exchanger). From either gas/liquid separator 109 or BHP collector 106, the separated BHP is then recirculated to BHP supply 102 for further use in the generation of SDO.

In one example, BHP supply 102 provides an aqueous mixture of hydrogen peroxide and a base. The base component may be selected from alkaline bases including but not limited to potassium hydroxide (KOH), sodium hydroxide (NaOH), and lithium hydroxide (LiOH). Preferably, KOH provides advantages such as low temperature and high concentration. In a further example, BHP can refer to an aqueous mixture of about 70 wt % hydrogen peroxide and about 45 wt % KOH.

Chlorine supply 104 provides chlorine gas and, optionally, an inert gas such as argon, nitrogen, or helium, to be injected into the reaction chamber of generator 110 via a gas injector 105 to allow high total pressure operation of the device.

With the use of KOH in one example, the BHP and chlorine reactants undergo a reaction in generator 110 to generate SDO following reaction equation (1) below.

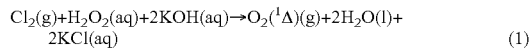

$$Cl_2(g) + H_2O_2(aq) + 2KOH(aq) \rightarrow O_2(^1\Delta)(g) + 2H_2O(l) + 2KCl(aq) \quad (1)$$

Generator 110 produces the SDO energy carrier through a reaction of an aqueous mixture of hydrogen peroxide and potassium hydroxide (in this example the BHP), with gas-phase chlorine. Byproducts of this reaction are a salt (in this case potassium chloride), water, and heat. The two-phase reaction shown in equation (1) is very exothermic, releasing most of the energy as heat into the BHP solution (110 kJ/mol) and maintaining the rest in an electronically excited state of oxygen called singlet delta oxygen.

As noted above, the BHP in many laser systems, (e.g., the ATL and ABL systems) is produced by mixing $H_2O_2$ with a base, such as KOH. The ratio of $OOH^-$ to $H_2O_2$ is critical to determining the BHP formulation and providing a desired concentration of BHP. BHP can also be regenerated from "spent" BHP (as is done in EC-COIL) through the use of an electrochemical cell, as will be described in more detail below with respect to FIG. 5.

Figure 2:
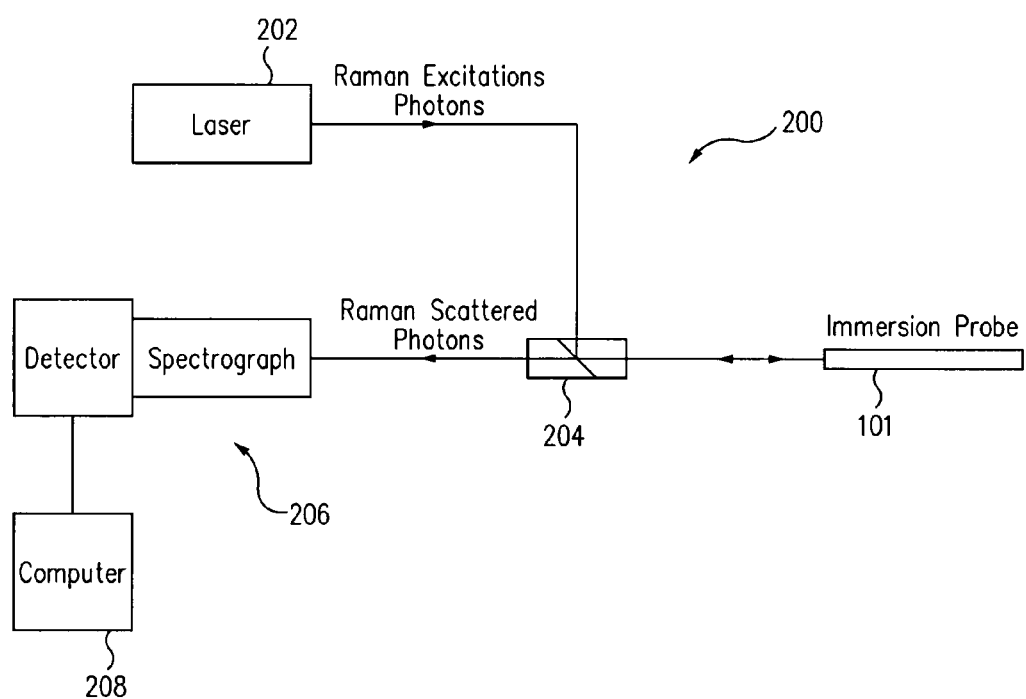
FIG. 2 shows a block diagram illustrating a solution monitoring system in accordance with an embodiment of the present invention.

As an example of how a solution monitoring system may be used with a COIL in accordance with an embodiment of the present invention, an immersion probe 101 is shown at three locations within the COIL system—BHP supply 102, BHP collector 106, and separator 109. In accordance with an embodiment of the present invention, a solution monitoring system including immersion probe 101 is shown in FIG. 2 and described in more detail below. It is noted that the solution monitoring system and method of the present invention may be used in other applications than a COIL, such as with paper production systems and other systems that utilize solutions including hydrogen peroxide. Immersion probe 101 may also be placed in various reservoirs or containers holding the solution of interest to be characterized.

Referring now to FIG. 2, a block diagram is shown illustrating a solution monitoring system 200 in accordance with an embodiment of the present invention. A laser 202 provides Raman excitation photons for the solution to be analyzed (not shown) and is operably coupled to immersion probe 101, in one example via an optical fiber. Immersion probe 101 delivers the Raman excitation photons from the laser to the solution and also is capable of collecting Raman scattered photons from the solution of interest. Immersion probe 101 is operably coupled to a spectrometer 206 via an optical fiber for transmission of the collected Raman scattered photons to spectrometer 206. A beam splitter 204 may operably couple laser 202, immersion probe 101, and spectrometer 206. A computer 208 may also be operably coupled to spectrometer 206.

Although laser 202 is not limited to a specific laser, examples of applicable lasers include a green, red, or near-infrared laser. Further examples of applicable lasers include Nd:YAG 106 nm and 532 nm lasers. Preferably, laser 202 has a narrow line width and will not be absorbed by or fluoresce the solution of interest, thereby allowing for measurement of the Raman effect in the solution.

In one example, immersion probe 101 includes a plurality of optical fibers for transmitting and receiving photons and is provided to both deliver the excitation laser light and to collect and transmit the Raman scattered photons to the imaging spectrometer. Applicable immersion probes, with no intent to limit the invention thereby, are available from Kaiser Optical Systems, Inc. of Ann Arbor, Mich.

Beam splitter 204 allows for a laser beam from laser 202 to pass along a fiber and also for Raman scattered photons at shifted wavelengths from immersion probe 101 to pass through another optical fiber coupled to spectrometer 206.

In one example, spectrometer 206 is any applicable optical instrument for measuring properties of light over a portion of the electromagnetic spectrum, in which received light diffracts off a diffraction grating and is dispersed into its components. The dispersed light falls onto a detector which measures the light intensity. The result of this is a measurement of light intensity as a function of wavelength. The measured variable may include but is not limited to light intensity, polarization state, and other properties. The independent variable may include but is not limited to wavelength of the light, wavenumber, and electron volts.

The detector of spectrometer 206 may be one of a focal plane array, a charge-coupled device (CCD), and a photodetector array, for measuring and recording the Raman spectrums based upon the received Raman scattered photons from the solution of interest. Spectrometer 206 may separate incoming light according to its wavelength and record the resulting spectrum in the detector. For example, spectrometer 206 may separate or resolve two Raman emission peaks that are in close proximity, for example within about 32 $cm^{-1}$ (e.g., the Raman shift for $H_2O_2$ and $HO_2^-$ is 877 $cm^{-1}$ and 845 $cm^{-1}$, respectively). Spectrometer 206 may also transform an incoming time-domain waveform into a frequency-domain (or related) spectrum, or generally a sequence of such spectra. In one example, with no intent to limit the invention thereby, applicable spectrometers are available from Kaiser Optical Systems, Inc. of Ann Arbor, Mich.

In one example, computer 208 may include a variety of typical computers, and in one example is a typical personal computer including a general or special purpose processor, with network capabilities. In one example, computer 208 comprises a CPU, a memory, and a network adapter, which are interconnected by a bus. Other conventional means, such as a display, a keyboard, a printer, a bulk storage device, and a ROM, may also be connected to the bus. The memory may store network and telecommunications programs and an operating system (OS).

Efficiencies for the immersion probe, the detector, and the spectrometer (e.g., grating efficiency) are preferably optimized for collecting, transmitting, and measuring the Raman scattered photons.

Figure 3A:
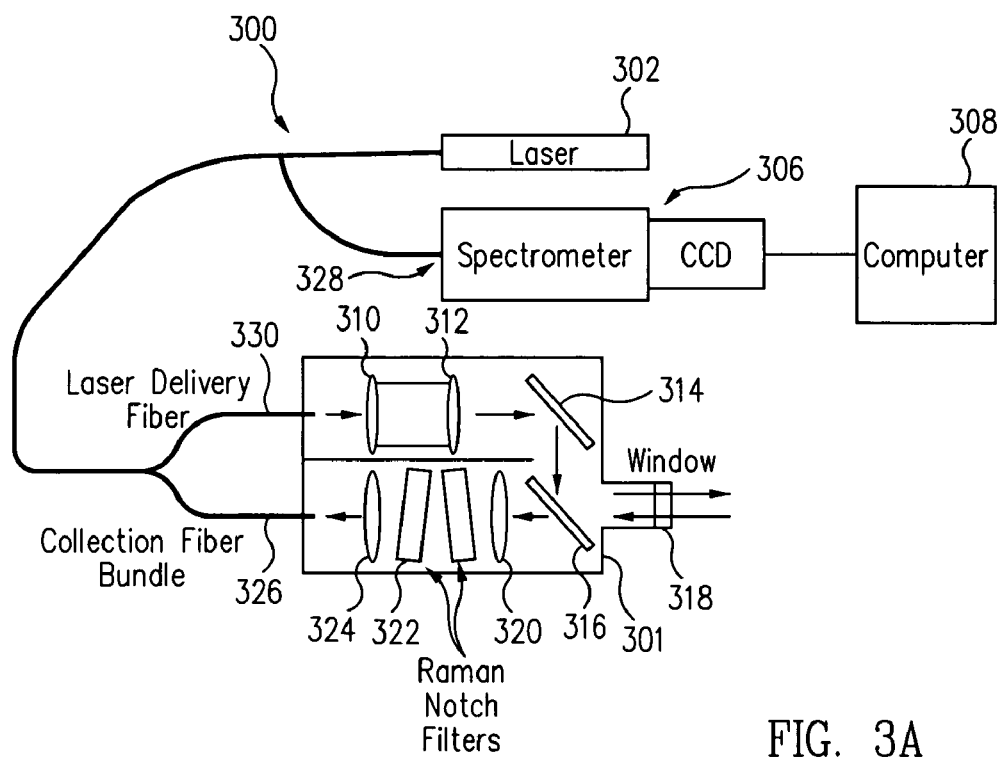
FIG. 3A shows a diagram illustrating another solution monitoring system in accordance with another embodiment of the present invention.
Figure 3B:
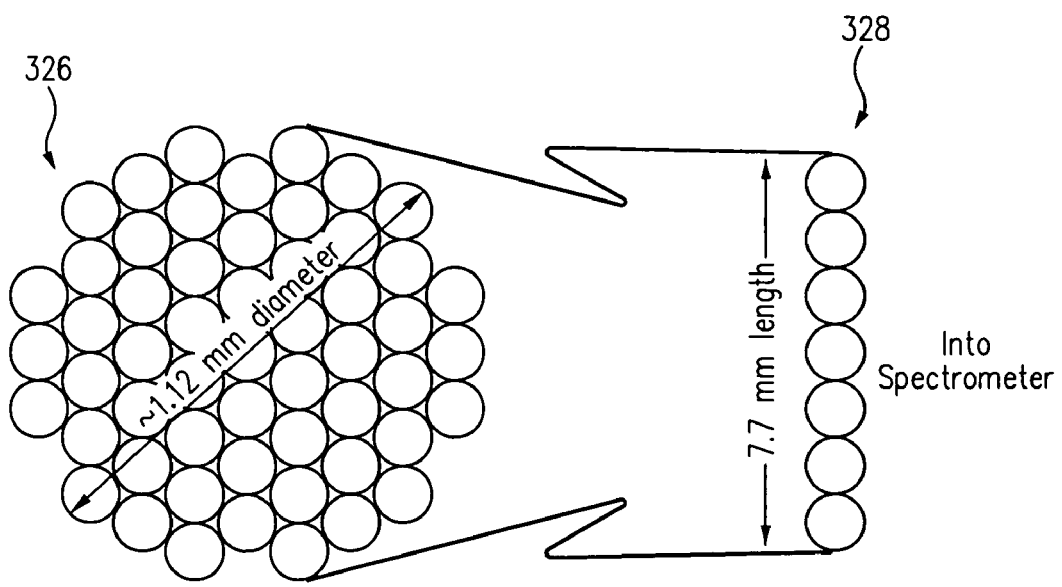
FIG. 3B shows the ends of a collection fiber bundle in accordance with an embodiment of the present invention.

Referring now to FIGS. 3A and 3B, another solution monitoring system 300 in accordance with another embodiment of the present invention is shown in FIG. 3A, and ends of a collection fiber bundle 326 are illustrated in FIG. 3B in accordance with an embodiment of the present invention.

A laser 302, a spectrometer 306, and a computer 308 are similar in function and structure to laser 202, spectrometer 206, and computer 208, respectively, and descriptions above with regard to laser 202, spectrometer 206, and computer 208 may similarly apply to laser 302, spectrometer 306, and computer 308, respectively.

Laser 302 provides Raman excitation photons for the solution to be analyzed (not shown) and is operably coupled to a laser delivery fiber 330. Light from laser delivery fiber 330 is sent through a collimating lens 310 and a focusing lens 312 and reflected from a mirror 314 to a beam splitter 316. Focused light from beam splitter 316 is sent through window 318, thereby delivering Raman excitation photons from the laser to the solution. Scattered light from the solution enters through window 318 and passes through beam splitter 316 to a collimating lens 320. The light from collimating lens 320 is filtered by Raman notch filters 322 to only pass Raman scattered photons (and filter out light at the laser wavelength). The Raman scattered photons are then focused by a focusing lens 324 and passed to a collection fiber bundle 326, which is operably coupled to spectrometer 306. In one embodiment, the elements housed within housing 301 may be used as a portion of immersion probe 101 (FIG. 2).

FIG. 3B shows an example of a light collecting end of collection fiber bundle 326 including 55 optical fibers with each fiber having a 140 micron core bundled together in a substantially cylindrical shape having a diameter of about 1 mm. Collection fiber bundle 326 collects Raman scattered photons and delivers the photons to spectrometer 306. At end 328 of collection fiber bundle 326, all the fibers (e.g., 55) are aligned through a slit for delivery of the collected light to spectrometer 306. For illustration purposes, only seven fiber ends are shown but typically all fibers of collection fiber bundle 326 will be aligned, in this example measuring a length of about 7.7 mm.

Figure 4:
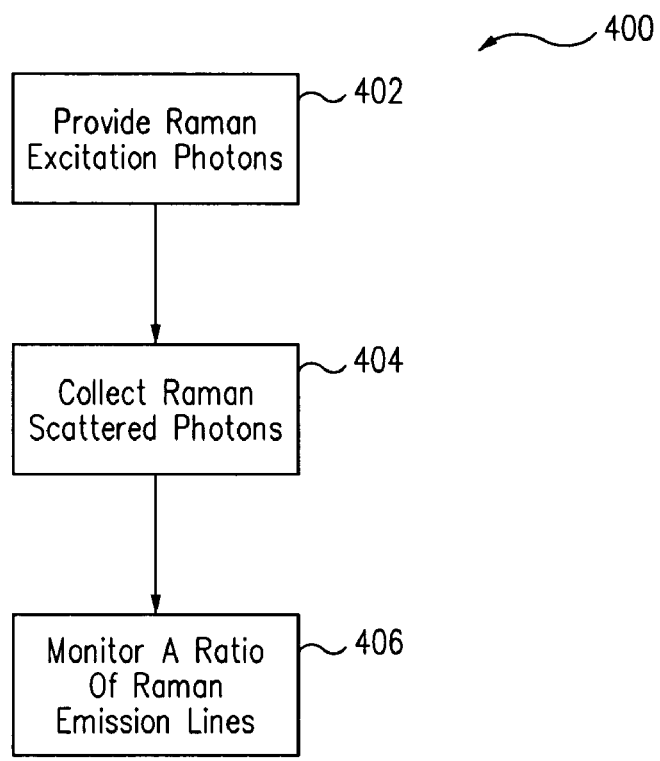
FIG. 4 shows a flowchart of a method for monitoring a solution including hydrogen peroxide in accordance with an embodiment of the present invention.

Referring now to FIG. 4, a flowchart of a method 400 for monitoring a solution including hydrogen peroxide is shown in accordance with an embodiment of the present invention. At step 402, Raman excitation photons are provided, for example by laser 202 and immersion probe 101 of FIG. 2, to a solution of interest to be monitored or characterized. At step 404, Raman scattered photons from the solution of interest are collected for subsequent measurement, for example by immersion probe 101 of FIGS. 1 through 3. At step 406, the Raman scattered photons are measured, for example by spectrometer 206 of FIG. 2, and more particularly in one example, a ratio of Raman emission lines in close proximity (e.g., within about 32 $cm^{-1}$ apart) is monitored for characterizing the solution (e.g., for concentration of desired components of the solution, or for molarity of BHP as it is being consumed to produce singlet delta oxygen or as it is being produced during a regeneration process).

In one example, the present invention permits BHP concentration to be monitored both in situ and in real-time by measuring the ratio of Raman emission lines in close proximity to one another at 845 $cm^{-1}$ for $OOH^-$ and at 875 $cm^{-1}$ for $H_2O_2$, reactants critical in the production of BHP. Advantageously, the close proximity of the Raman peaks (845 $cm^{-1}$ compared to 875 $cm^{-1}$) permits the concentration of $OOH^-$ and $H_2O_2$ to be monitored without having to account for optical train (transmission, grating, and detector sensitivity and efficiency) differences due to wavelength.

Figure 5:
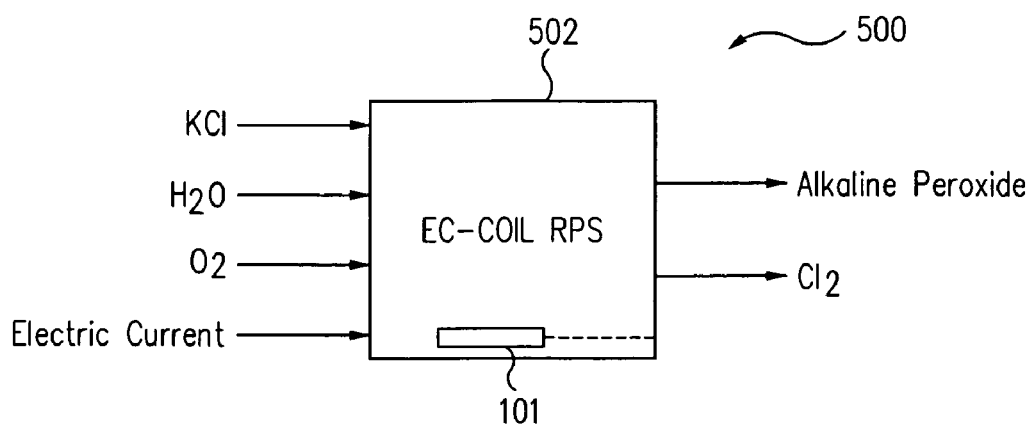
FIG. 5 shows a diagram illustrating a fuel regeneration system including a solution monitor in accordance with an embodiment of the present invention.

In accordance with another embodiment of the present invention, an implementation with an EC-COIL fuel regeneration system 500 will now be described with respect to FIG. 5. In an EC-COIL system, BHP is regenerated by adding alkaline peroxide to "spent" BHP. The present invention may thus be used to monitor and/or control in real time the production of regenerated BHP when using alkaline peroxide by monitoring the $OOH^-$ to $OH^-$ ratio.

The EC-COIL fuel regeneration system recovers the waste products of the COIL laser and reacts them in an electrochemical cell 502, known as the Reagent Production System (RPS), to produce fresh laser fuel. The EC-COIL RPS causes the reverse of reaction equation (1) to occur as follows:

$$2KCl + 2H_2O + O_2 \rightarrow 2KOH + H_2O_2 + Cl_2 \quad (2)$$

The products are chlorine gas and an aqueous solution of KOH and $H_2O_2$, known as alkaline peroxide. The KOH and $H_2O_2$ react to form the aqueous ions $OH^-$, $HO_2^-$, and $K^+$. In order to regenerate the laser fuel exactly, the RPS must produce KOH and $H_2O_2$ in a two-to-one mole ratio, respectively. The resulting alkaline peroxide would contain $OH^-$ and $HO_2^-$ in a one-to-one ratio, respectively, as follows:

$$2KOH(aq) + H_2O_2(aq) \rightarrow 2K^+ + OH^- + HO_2^- + H_2O \quad (3)$$

The ratio of $OH^-$ to $HO_2^-$ varies with the operating conditions of the RPS. The present invention can thus measure the ratio of $OH^-$ (at 1630 $cm^{-1}$) to $HO_2^-$ (at 845 $cm^{-1}$) in real time providing a diagnostic tool for optimizing the operating conditions to achieve the desired $OH^-$ to $HO_2^-$ ion mole ratio of one-to-one.

The present invention is also applicable for monitoring alternative COIL laser fuels including but not limited to hydrogen peroxide and hypochlorites including lithium hypochlorite. For these alternative fuels, both the $OOH^-$ ion and the hypochlorite ion ($OCl^-$) may be monitored.

The system and method of the present invention advantageously provides for substantially real time and in situ monitoring of solutions including hydrogen peroxide, and more particularly laser fuel solutions including hydrogen peroxide and one of a base and a hypochlorite.

Embodiments described above illustrate but do not limit the invention. It should also be understood that numerous modifications and variations are possible in accordance with the principles of the present invention. For example, different lasers, immersion probes, and spectrometers may be used to apply Raman spectroscopy to various solutions for monitoring and characterizing of the solutions. Accordingly, the scope of the invention is defined only by the following claims.

We claim:

1. A chemical laser system, comprising:
   a liquid reactant supply including:
      a laser for providing excitation photons to a liquid reactant of a chemical laser;
      an immersion probe within the liquid reactant for transmitting Raman scattered photons; and
      a spectrometer operably coupled to the immersion probe for measuring the Raman scattered photons transmitted by the immersion probe;
   a generator including a liquid inlet for flowing the liquid reactant from the liquid reactant supply and a gas inlet for flowing a gas reactant, the generator allowing a reaction between the gas reactant and the liquid reactant to generate singlet delta oxygen;
   a nozzle operably coupled to an outlet of the generator;
   a lasing species supply operably coupled to the nozzle; and
   a cavity operably coupled to an outlet of the nozzle for stimulated emission of an electronically excited lasing species.

2. The system of claim 1, wherein the immersion probe is operably coupled to the laser and delivers the excitation photons from the laser to the liquid reactant.

3. The system of claim 1, wherein the immersion probe collects the Raman scattered photons for subsequent transmission to the spectrometer.

4. The system of claim 1, wherein the immersion probe includes a plurality of optical fibers for transmitting and receiving photons.

5. The system of claim 1, wherein the liquid reactant includes hydrogen peroxide.

6. The system of claim 5, wherein the liquid reactant further includes one of a base and a hypochlorite.

7. The system of claim 1, wherein the spectrometer measures Raman emissions lines for at least one of $OOH^-$, $OH^-$, $OCl^-$, and $H_2O_2$.

8. The system of claim 1, wherein the spectrometer measures Raman emission lines at about 845 $cm^{-1}$ for $OOH^-$ and Raman emission lines at about 875 $cm^{-1}$ for $H_2O_2$.

9. The system of claim 1, wherein the spectrometer includes a detector for recording a Raman spectrum resulting from the Raman scattered photons transmitted by the immersion probe.

10. The system of claim 9, wherein the detector is one of a focal plane array detector and a charge-coupled device (CCD) detector.

11. The system of claim 1, further comprising a beam splitter operably coupling the laser, the immersion probe, and the spectrometer.

12. The system of claim 1, wherein the lasing species is selected from the group consisting of iodine ($I_2$) and hydrogen fluoride (HF).

13. The system of claim 1, further comprising a diffuser operably coupled to an outlet of the cavity.

14. The system of claim 13, further comprising a vacuum system operably coupled to an outlet of the diffuser.

15. The system of claim 13, further comprising an accumulator operably coupled to an outlet of the diffuser for isolating residual products including chlorine.

16. A method of monitoring a liquid reactant of a chemical laser comprising:
   providing Raman excitation photons to a liquid reactant of a chemical laser including basic hydrogen peroxide;
   collecting Raman scattered photons from the liquid reactant; and
   monitoring a ratio of Raman emission lines to determine characteristics of the liquid reactant outputting a signal representative of the ratio.

17. The method of claim 16, wherein the Raman excitation photons are provided to the liquid reactant by a laser and an immersion probe and further wherein the Raman scattered photons are collected by the immersion probe.

18. The method of claim 16, wherein the Raman emission lines are in close proximity to one another.

19. The method of claim 16, wherein the ratio of Raman emission lines includes at least one of $OOH^-$, $OH^-$, $OCl^-$, and $H_2O_2$.

20. The method of claim 16, wherein the ratio of Raman emission lines includes Raman emission lines at about 845 $cm^{-1}$ for $OOH^-$ and Raman emission lines at about 875 $cm^{-1}$ for $H_2O_2$.

* * * * *